(12) United States Patent
De Villiers et al.

(10) Patent No.: US 7,637,913 B2
(45) Date of Patent: Dec. 29, 2009

(54) SPINAL MIDLINE INDICATOR

(75) Inventors: Malan De Villiers, Irene (ZA); Ulrich Reinhard Hähnle, Saxonwold (ZA)

(73) Assignee: SpinalMotion, Inc., Mountain View, CA (US)

( * ) Notice: Subject to any disclaimer, the term of this patent is extended or adjusted under 35 U.S.C. 154(b) by 565 days.

(21) Appl. No.: 11/187,733

(22) Filed: Jul. 21, 2005

(65) Prior Publication Data

US 2006/0029186 A1     Feb. 9, 2006

Related U.S. Application Data

(63) Continuation of application No. PCT/IB2004/000170, filed on Jan. 26, 2004.

(30) Foreign Application Priority Data

Jan. 31, 2003     (ZA)     ................... 2003/0874

(51) Int. Cl.
A61B 17/56     (2006.01)
A61B 5/05      (2006.01)
A61F 2/44      (2006.01)

(52) U.S. Cl. ................ 606/99; 600/424; 600/426

(58) Field of Classification Search ............. 606/61, 606/90, 139, 93, 101, 898, 130, 57, 89, 279, 606/86 R, 102, 97, 80, 99, 240, 85, 280, 207, 606/105; 600/439, 587, 407, 429, 424; 128/898; 623/17, 60, 61, 17.11–17.16, 79, 86, 102; 378/162, 37

See application file for complete search history.

(56) References Cited

U.S. PATENT DOCUMENTS

| 3,486,505 A | 12/1969 | Morrison |
| 4,759,766 A | 7/1988 | Buettner-Janz et al. |
| 4,863,477 A | 9/1989 | Monson |
| 4,997,432 A | 3/1991 | Keller |
| 5,035,716 A | 7/1991 | Downey |
| 5,071,437 A | 12/1991 | Steffee |
| 5,122,130 A | 6/1992 | Keller |
| 5,195,526 A | 3/1993 | Michelson |
| 5,258,031 A | 11/1993 | Salt et al. |
| 5,314,477 A | 5/1994 | Marnay |
| 5,370,697 A | 12/1994 | Baumgartner |

(Continued)

FOREIGN PATENT DOCUMENTS

EP     0333990 A2     9/1989

(Continued)

OTHER PUBLICATIONS

Karin Buttner-Janz, The Development of the Artificial Disc, Introduction, 1989, pp. 1-18, Library of Congress Catalogue No. 92-75582, ISBN 0-9635430-0-8.

(Continued)

*Primary Examiner*—Eric F Winakur
*Assistant Examiner*—Lawrence N Laryea
(74) *Attorney, Agent, or Firm*—Townsend and Townsend and Crew LLP

(57) ABSTRACT

A spinal midline indicator (10) has a body (14) of radiolucent material for insertion between adjacent vertebrae (18, 20) and a radiographic marker (12) located centrally with the body to indicate the position of the spinal midline (22) in anterior-posterior images when the body is centrally located between the vertebrae. The radiographic marker is typically an elongate metal handle. The body may carry secondary radiographic markers (16) on opposite sides of and equidistant from the handle so that the handle indicates the position of the spinal midline when the body is placed centrally between the vertebrae.

20 Claims, 2 Drawing Sheets

U.S. PATENT DOCUMENTS

| | | | |
|---|---|---|---|
| 5,394,457 | A | 2/1995 | Leibinger et al. |
| 5,401,269 | A | 3/1995 | Buttner-Janz et al. |
| 5,489,307 | A * | 2/1996 | Kuslich et al. ............. 128/898 |
| 5,507,816 | A | 4/1996 | Bullivant |
| 5,534,030 | A | 7/1996 | Navarro et al. |
| 5,556,431 | A | 9/1996 | Buttner-Janz |
| 5,674,296 | A | 10/1997 | Bryan et al. |
| 5,676,701 | A | 10/1997 | Yuan et al. |
| 5,676,702 | A | 10/1997 | Ratron |
| 5,702,450 | A | 12/1997 | Bisserie |
| 5,797,909 | A | 8/1998 | Michelson |
| 5,824,094 | A | 10/1998 | Serhan et al. |
| 5,865,846 | A | 2/1999 | Bryan et al. |
| 5,989,291 | A | 11/1999 | Ralph et al. |
| 6,001,130 | A | 12/1999 | Bryan et al. |
| 6,022,376 | A | 2/2000 | Assell et al. |
| 6,039,763 | A | 3/2000 | Shelokov |
| 6,096,038 | A | 8/2000 | Michelson |
| 6,139,579 | A | 10/2000 | Steffee et al. |
| 6,156,067 | A | 12/2000 | Bryan et al. |
| 6,162,252 | A | 12/2000 | Kuras et al. |
| 6,224,607 | B1 | 5/2001 | Michelson |
| 6,235,030 | B1 | 5/2001 | Zuckerman et al. |
| 6,261,296 | B1 | 7/2001 | Aebi et al. |
| 6,315,797 | B1 | 11/2001 | Middleton |
| 6,322,567 | B1 * | 11/2001 | Mittelstadt et al. .......... 606/130 |
| 6,348,071 | B1 | 2/2002 | Steffee et al. |
| 6,368,350 | B1 | 4/2002 | Erickson et al. |
| 6,416,551 | B1 | 7/2002 | Keller |
| 6,478,800 | B1 | 11/2002 | Fraser et al. |
| 6,562,047 | B2 | 5/2003 | Ralph et al. |
| 6,592,624 | B1 | 7/2003 | Fraser et al. |
| 6,599,294 | B2 | 7/2003 | Fuss et al. |
| 6,607,558 | B2 | 8/2003 | Kuras |
| 6,648,895 | B2 * | 11/2003 | Burkus et al. ................. 606/90 |
| 6,652,533 | B2 | 11/2003 | O'Neil |
| 6,666,866 | B2 | 12/2003 | Mertz et al. |
| 6,689,132 | B2 | 2/2004 | Biscup |
| 6,706,068 | B2 | 3/2004 | Ferree |
| 6,712,819 | B2 * | 3/2004 | Zucherman et al. ....... 606/86 A |
| 6,712,825 | B2 | 3/2004 | Aebi et al. |
| 6,723,097 | B2 * | 4/2004 | Fraser et al. ................. 606/61 |
| 6,740,118 | B2 | 5/2004 | Eisermann et al. |
| 6,814,737 | B2 | 11/2004 | Cauthan |
| 6,875,213 | B2 | 4/2005 | Michelson |
| 6,963,071 | B2 | 11/2005 | Bristol |
| 7,025,787 | B2 | 4/2006 | Bryan et al. |
| 7,060,073 | B2 * | 6/2006 | Frey et al. ..................... 606/85 |
| 7,207,991 | B2 * | 4/2007 | Michelson ................ 606/86 A |
| 2001/0016773 | A1 | 8/2001 | Serhan et al. |
| 2001/0029377 | A1 | 10/2001 | Aebi et al. |
| 2002/0022845 | A1 * | 2/2002 | Zdeblick et al. ............... 606/80 |
| 2002/0035400 | A1 | 3/2002 | Bryan et al. |
| 2002/0068936 | A1 * | 6/2002 | Burkus et al. ................. 606/57 |
| 2002/0128715 | A1 | 9/2002 | Bryan et al. |
| 2002/0198532 | A1 | 12/2002 | Michelson |
| 2003/0045884 | A1 * | 3/2003 | Robie et al. ................... 606/90 |
| 2003/0074076 | A1 | 4/2003 | Ferree et al. |
| 2003/0100951 | A1 | 5/2003 | Serhan et al. |
| 2003/0125739 | A1 * | 7/2003 | Bagga et al. ................... 606/61 |
| 2003/0191536 | A1 | 10/2003 | Ferree |
| 2003/0199982 | A1 | 10/2003 | Bryan |
| 2003/0204261 | A1 | 10/2003 | Eisermann et al. |
| 2003/0208271 | A1 | 11/2003 | Kuras |
| 2004/0024407 | A1 | 2/2004 | Ralph |
| 2004/0024410 | A1 * | 2/2004 | Olson et al. ................... 606/93 |
| 2004/0030391 | A1 | 2/2004 | Ferree |
| 2004/0073312 | A1 | 4/2004 | Eisermann et al. |
| 2004/0143270 | A1 | 7/2004 | Zucherman et al. |
| 2004/0176843 | A1 | 9/2004 | Zubok et al. |
| 2005/0043800 | A1 | 2/2005 | Paul et al. |
| 2005/0085917 | A1 | 4/2005 | Marnay et al. |
| 2005/0107881 | A1 | 5/2005 | Alleyne et al. |
| 2005/0149189 | A1 | 7/2005 | Mokhtar et al. |
| 2005/0192586 | A1 | 9/2005 | Zuckerman et al. |
| 2005/0197706 | A1 | 9/2005 | Hovorka et al. |
| 2005/0261772 | A1 | 11/2005 | Filippi et al. |
| 2006/0041313 | A1 | 2/2006 | Allard et al. |

FOREIGN PATENT DOCUMENTS

| | | | |
|---|---|---|---|
| EP | 0560141 | A1 | 9/1993 |
| EP | 0560140 | A1 | 1/1994 |
| EP | 0591712 | A1 | 4/1994 |
| EP | 1142544 | A1 | 10/2001 |
| EP | 1153582 | A2 | 11/2001 |
| EP | 1250898 | A1 | 10/2002 |
| EP | 1306064 | A1 | 5/2003 |
| EP | 1344493 | A1 | 9/2003 |
| EP | 1344506 | A1 | 9/2003 |
| EP | 1344507 | A1 | 9/2003 |
| EP | 1344508 | A1 | 9/2003 |
| EP | 1417940 | A1 | 5/2004 |
| WO | WO 01/01893 | A1 | 1/2001 |
| WO | WO 2004/026187 | A1 | 4/2004 |
| WO | WO 2005/053580 | A1 | 6/2005 |

OTHER PUBLICATIONS

Office Action of Japanese Patent Application No. 2006-502359, dated Jul. 2, 2009, 5 pages total. [English Translation Included].

* cited by examiner

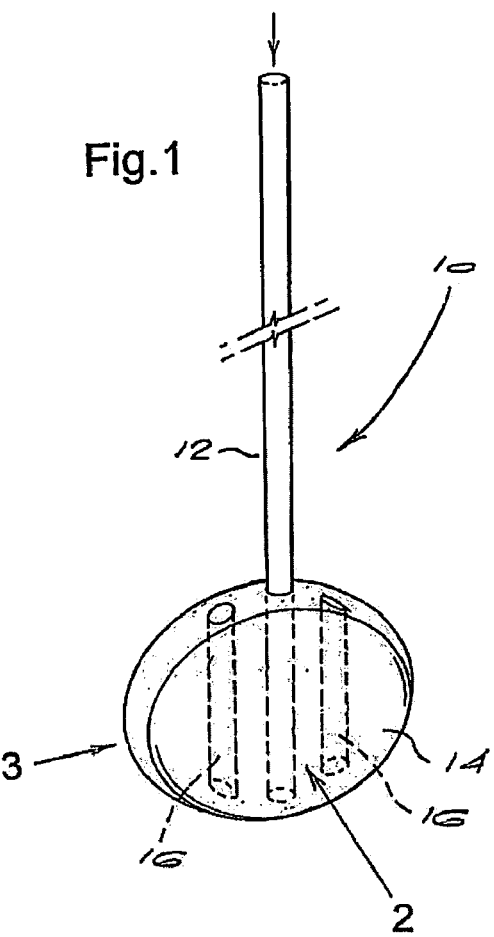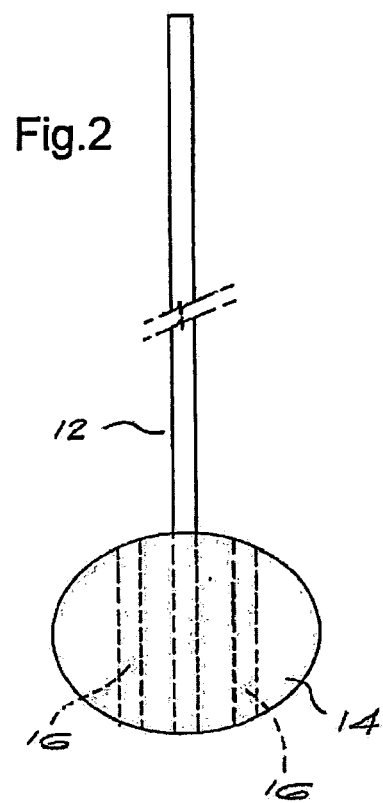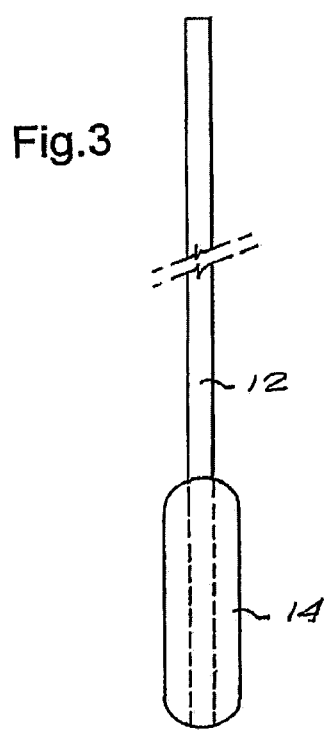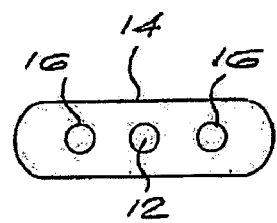

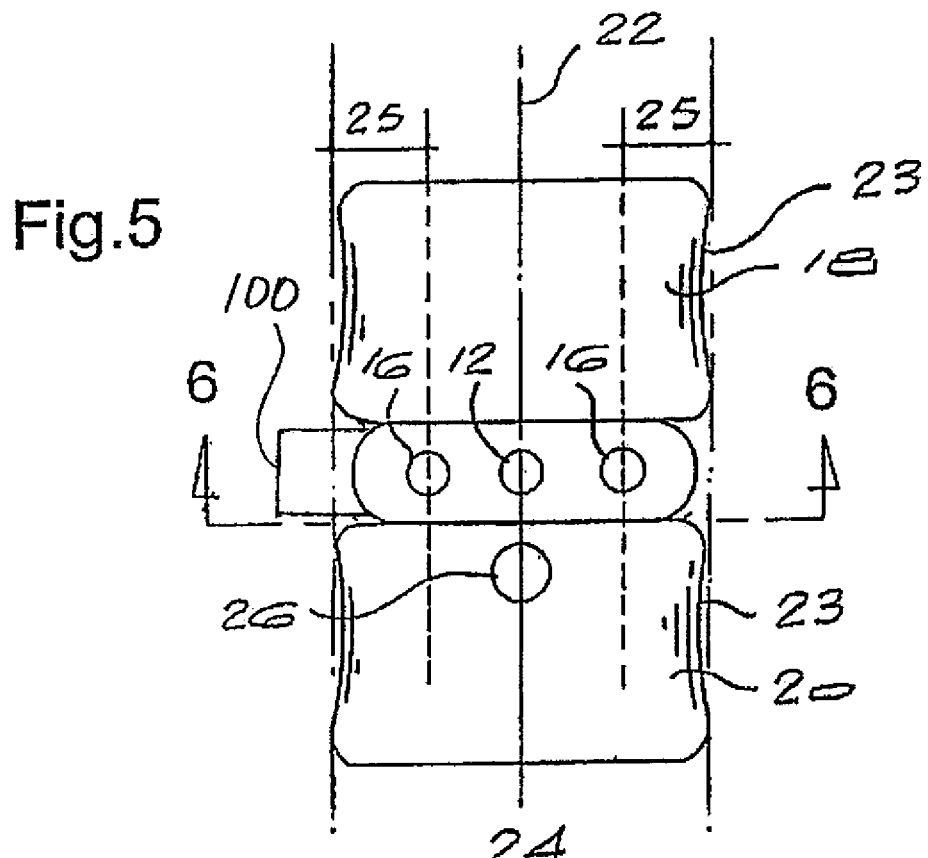
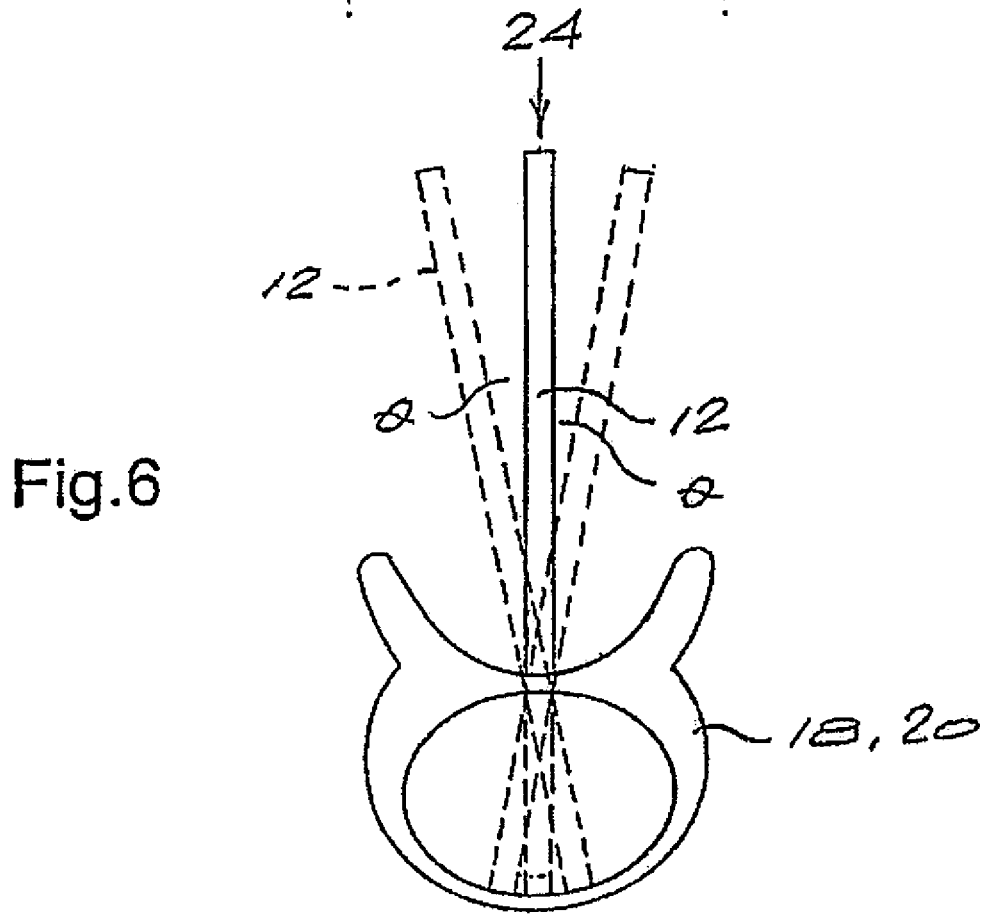

SPINAL MIDLINE INDICATOR

CROSS-REFERENCES TO RELATED APPLICATIONS

This application is a continuation of International Application PCT/IB2004/000170, filed on Jan. 26, 2004, which claimed priority from South African application 2003/0874, filed on Jan. 31, 2003, the full disclosures of which are incorporated herein by reference.

BACKGROUND OF THE INVENTION

This invention relates to a spinal midline indicator.

It is important for a surgeon performing an ALIF (anterior lumbar interbody fusion) or ACIF (anterior cervical interbody fusion) cage or spinal disc replacement procedure to be able accurately to establish the centre- or midline of the spine. It is only once the surgeon has correctly established the position of the spinal midline that he is able to place the cage or spinal disc accurately on that midline. ff-centre placement will result in eccentric loading and possible early failure or accelerated wear.

At present, surgeons attempt to establish the spinal midline by visual inspection of an A-P (anterior-posterior) image. However this is often inaccurate, and can lead to subsequent off-centre placement of the cage or disc with potential disadvantages as described above.

The present invention seeks to provide an instrument which will facilitate accurate establishment of the spinal midline.

BRIEF SUMMARY OF THE INVENTION

According to the present invention there is provided a spinal midline indicator comprising a body of radiolucent material for insertion between adjacent vertebrae and a radiographic marker associated centrally with the body to indicate, in an anterior-posterior radiographic image, the position of the spinal midline when the body is appropriately located between the vertebrae. Conveniently the radiographic marker is an elongate handle which is connected to the body to facilitate placement of the body between the vertebrae and which is made of a radiographic material, i.e., a material which is substantially opaque to radiographic (fluoroscopic) imaging.

In the preferred embodiment, the body carries, in addition to the handle which serves as a first radiographic marker, two or more secondary radiographic markers on opposite sides of and equidistant from the first marker, whereby the first marker indicates the position of the spinal midline when the body is placed centrally between the vertebrae and the secondary markers are seen in the radiographic image to be equidistant from lateral edges of the vertebrae.

Further according to the invention there is provided a method of identifying a spinal midline which comprises the steps of inserting the body of a spinal midline indicator as summarized above between adjacent spinal vertebrae, manipulating the body so that the radiographic marker is seen in a radiographic image to be on the spinal midline, and, using the position of the radiographic marker as a guide, applying a marking, eg. a pin, to a vertebra to indicate the midline.

Other features of the invention are set forth in the appended claims.

BRIEF DESCRIPTION OF THE DRAWINGS

The invention will now be described in more detail, by way of example only, with reference to the accompanying drawings.

FIG. 1 shows a perspective view of a spinal midline indicator according to the invention;

FIG. 2 shows a side view of the indicator in the direction of the arrow 2 in FIG. 1;

FIG. 3 shows a side view of the indicator in the direction of the arrow 3 in FIG. 1;

FIG. 4 shows an end view of the indicator in the direction of the arrow 4 in FIG. 1;

FIG. 5 diagrammatically illustrates the indicator in use; and

FIG. 6 shows a diagrammatic cross-section at the line 6-6 in FIG. 5.

DETAILED DESCRIPTION OF THE INVENTION

The spinal midline indicator 10 seen in FIGS. 1 to 4 includes an elongate handle 12 and a body 14 carried centrally at one end of the handle. The handle is made of a radiographic material, i.e. one which is opaque to radiation in the radiowave part of the spectrum, including X-radiation. The handle may, for instance, be made of stainless steel or titanium. The handle 12 extends substantially through the body 14. The body 14 is made of a radiolucent material, i.e. one which is at least to some degree transparent to the radiation. The body may, for instance, be made of PEEK (polyetheretherketone) or UHMWPE (ultra-high molecular weight polyethylene).

Embedded in the body 14 are two elongate markers 16, also of radiographic material such as stainless steel or titanium. The markers 16 are aligned parallel to the handle 12 and are located on opposite sides of, and equidistant from the handle.

FIG. 5 diagrammatically illustrates, in an anterior view, adjacent upper and lower vertebrae 18 and 20 respectively. As explained above it is important, during an ALIF or ACIF cage or spinal disc replacement procedure carried out anteriorly, for the surgeon to be able accurately to establish the spinal midline, indicated by the line 22, since it is centrally on this line that the replacement disc or cage must be placed. The procedure is typically carried out, with the patient lying prone and flat on his back, through a frontal incision.

In order to establish the midline 22, the surgeon aligns the handle 12 at a vertical orientation and uses it to insert the body 14 between the vertebrae 18 and 20. It will be understood that a separate instrument 100 is used to hold the vertebrae apart for this insertion to take place. An attempt is made to orientate the body centrally with the handle 12 vertical, thereby to ensure that the handle correctly indicates the midline 22.

An X-ray photograph or radiographic image is taken in the vertical anterior-posterior direction. In this radiographic image the handle 12, markers 16 and vertebrae 18,20 will be visible. By ensuring that the markers 16 are equidistantly laterally spaced from the osseous edges 23 of the vertebrae, i.e. that the distance 25 is the same on both sides, the surgeon can ensure that the body 14 and handle 12 are centrally positioned. It will be understood that during this procedure, the handle 12 itself operates as a radiographic marker indicating a central position.

It will also be understood that if the handle 12 and markers 16 are aligned with the anterior-posterior direction in which the radiographic image is taken, they will appear in the radiographic image merely as dots of small lateral dimension. However if the handle is not perfectly aligned in the anterior-posterior, i.e. vertical direction, parallax effects will result in the handle and markers being seen as lines rather than dots.

This is illustrated in FIG. 6 in which the full lines show the handle 10 at the correct anterior-posterior or vertical orientation and the broken lines show it at orientations in which it is misaligned by an angle 9. It will be understood that in a radiographic image in the anterior-posterior direction indicated by the arrow 24, the handle 12 and markers 16 will appear as dots at the full line orientation but as short lines at the broken line orientations.

By consulting radiographic images and manipulating the indicator 10 as necessary in response to the information derived therefrom, the surgeon can ensure that the indicator is at the correct position and orientation. When the indicator is in the correct position and at the correct orientation, the handle 12 will lie in a vertical plane containing the midline 22. The surgeon can now use the handle as a positive indicator of that midline. The position of the radiographic marker can be used as a guide to apply a marking to a vertebra to indicate the midline. He can accurately mark the midline, for instance by knocking a pin 26 into one of the vertebrae.

Once the midline has been marked on one or both of the vertebrae, the indicator 10 is no longer required and can be removed for later re-use. The marker(s) then serve to indicate the midline 22 to enable subsequent, accurate positioning of the relevant prosthesis to take place.

What is claimed is:

1. A spinal midline indicator comprising:
   a body of radiolucent material for insertion between adjacent vertebrae;
   a radiographic marker disposed centrally within the body to indicate a position of the spinal midline when the body is located between the vertebrae in an anterior-posterior radiographic image, wherein the radiographic marker extends from the within the body and comprises an elongate handle made of a radiographic material and wherein the elongate handle is connected to the body to facilitate placement of the body between the vertebrae;
   wherein the body carries a first radiographic marker and at least two secondary radiographic markers on opposite sides of and equidistant from the first marker, whereby the first marker indicates the position of the spinal midline when the body is placed centrally between the vertebrae and the secondary markers are seen in the radiographic image to be equidistant from lateral edges of the vertebrae;
   wherein the first radiographic marker is an elongate handle which is connected to the body to facilitate placement of the body between the vertebrae and which is made of a radiographic material; and
   wherein the handle is made of stainless steel or titanium and is embedded in the body.

2. A spinal midline indicator according to claim 1 wherein the handle extends through the body.

3. A spinal midline indicator according to claim 2 wherein the secondary markers are elongate in shape and are parallel to the handle so that alignment of the markers relative to the anterior-posterior direction can be assessed in the radiographic image.

4. A spinal midline indicator according to claim 3 wherein the secondary markers are made of stainless steel or titanium.

5. A spinal midline indicator according to claim 4 wherein the secondary markers are embedded in the body.

6. A spinal midline indicator according to claim 5 wherein the secondary markers extend through the body.

7. A spinal midline indicator as in claim 1 wherein the body is made of PEEK or UHMWPE.

8. A spinal midline indicator as in claim 1 wherein the body has an elliptical shape and is of flat proportions.

9. A spinal midline indicator as in claim 1 wherein the handle extends substantially through the body.

10. A method of identifying a spinal midline which comprises
    providing a spinal midline indicator comprising a body of radiolucent material for insertion between adjacent vertebrae and a radiographic marker disposed centrally in the body to indicate the position of the spinal midline when the body is located between the vertebrae in an anterior-posterior radiographic image;
    inserting the body of the spinal midline indicator between the adjacent spinal vertebrae;
    manipulating the body so that the radiographic marker is seen in a radiographic image to be on the spinal midline; and
    using a position of the radiographic marker as a guide to apply a marking to a vertebra to indicate the midline.

11. A method according to claim 10 wherein the vertebra is marked by a pin.

12. A method of identifying a spinal midline for a fusion or disc replacement procedure, the method comprising:
    creating a frontal incision with a patient lying prone on his back;
    inserting a spinal midline indicator into a space between adjacent vertebrae, the spinal midline indicator including a body of radiolucent material and a radiographic marker formed as an elongated handle attached to and extending from the body;
    centering the radiographic marker while viewing the spinal midline indicator in a radiographic image; and
    marking the midline on at least one of the vertebrae.

13. A method according to claim 12, wherein the marking includes marking the midline on both adjacent vertebrae.

14. A method according to claim 12, wherein a separate instrument is used to hold the adjacent vertebrae apart.

15. A method of identifying a spinal midline, the method comprising:
    providing a spinal midline indicator comprising a body of radiolucent material and a radiographic marker disposed centrally in the body;
    inserting the body of the spinal midline indicator between two adjacent spinal vertebrae, such that the radiographic marker indicates the position of the spinal midline when the body is located between the vertebrae in an anterior-posterior radiographic image;
    manipulating the body so that the radiographic marker is seen in the anterior-posterior radiographic image to be on the spinal midline; and
    using a position of the radiographic marker to guide a mark applied to at least one of the two adjacent vertebra to indicate the spinal midline.

16. A method according to claim 15, wherein both of the adjacent vertebrae are marked.

17. A method according to claim 15, wherein a separate instrument is used to hold the adjacent vertebrae apart.

18. A method according to claim 15 wherein the at least one of the two adjacent vertebrae is marked by a pin.

19. A method according to claim 15, wherein the radiographic marker comprises a handle that extends from the body.

20. A method according to claim 15, wherein the radiographic marker is removed from between the adjacent spinal vertebrae and the mark is used to guide positioning of a prosthesis.

* * * * *

UNITED STATES PATENT AND TRADEMARK OFFICE
CERTIFICATE OF CORRECTION

PATENT NO.      : 7,637,913 B2  Page 1 of 1
APPLICATION NO. : 11/187733
DATED           : December 29, 2009
INVENTOR(S)     : De Villiers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 858 days.

Signed and Sealed this

Ninth Day of November, 2010

David J. Kappos
*Director of the United States Patent and Trademark Office*